United States Patent [19]

Della Bella et al.

[11] Patent Number: 4,840,936
[45] Date of Patent: Jun. 20, 1989

[54] PHARMACEUTICALLY USEFUL DERIVATIVES OF THIAZOLIDINE-4-CARBOXYLIC ACID

[75] Inventors: Davide Della Bella, Milan; Angelo Carenzi, Busto Arsizio; Dario Chiarino, Monza; Franco Pellacini, Sesto S. Giovanni, all of Italy

[73] Assignee: Zambon S.p.A., Milan, Italy

[21] Appl. No.: 72,569

[22] Filed: Jul. 13, 1987

[30] Foreign Application Priority Data

Jul. 14, 1986 [IT] Italy ................... 21112 A/86

[51] Int. Cl.$^4$ .................. C07D 277/06; C07D 417/06; A61K 31/425
[52] U.S. Cl. ......................... 514/18; 514/19; 514/365; 530/331; 548/200; 548/201
[58] Field of Search ............... 548/200, 201; 530/331; 514/365, 18, 19

[56] References Cited

U.S. PATENT DOCUMENTS 4,457,935 7/1984 Iwao .................. 548/201
4,457,936 7/1984 Draeger ................ 548/200

Primary Examiner—Robert Gerstl
Attorney, Agent, or Firm—Stevens, Davis, Miller & Mosher

[57] ABSTRACT

Compounds of formula

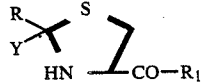

(I)

in which R, $R_1$ and Y have the meanings shown in the description, their preparation by condensing an aldehyde or a ketone with cysteine or a derivative thereof and their use in the pharmaceutical field.

The compounds of formula I possess antipyretic, antiinflammatory, mucolytic and analgesic activity together with a low capacity to cause gastric injuries.

The compounds of formula I, furthermore, are particularly useful in the treatment of ischemia and reperfusion syndromes.

17 Claims, No Drawings

PHARMACEUTICALLY USEFUL DERIVATIVES OF THIAZOLIDINE-4-CARBOXYLIC ACID

This invention relates to thiazolidine-4-carboxylic acid derivatives, and more specifically to thiazolidine-4-carboxylic acid derivatives substituted at 2-position and optionally at the carboxy group, and their salts with pharmacologically acceptable bases or acids.

This invention furthermore relates to the preparation of the said compounds and their use in the pharmaceutical field.

Various thiazolidine-4-carboxylic acid derivatives substituted at 2 position and having pharmaceutical action are known.

The Japanese patent application No. 82/128-625 (Chemical Abstracts, 97:2032316) describes some derivatives of thiazolidine-4-carboxylic acid which are substituted at 2-position, by an alkyl, phenyl, napthyl or a benzyl radical and show antitumoral activity.

The German Pat. No. 2,208,533 (Chemical Abstract, 80:3529s) describes derivatives of thiazolidine-4-carboxylic acid which are substituted at 2-position by an undecyl or a benzyl group and are endowed with bacteriostatic and fungistatic activity.

The carboxy group at 4-position in the said known compounds is always free or salified.

The new compounds of this invention have the following general formula

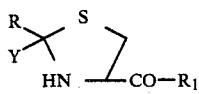

(I)

in which : Y is hydrogen, or methyl;
R is a radical selected from
  (6-methoxy)-2-napthyl)-methyl,
  1-(4-isobutylphenyl)-ethyl,
  1-(6-methoxy-2-napthyl)-ethyl,
  5-(2,4-difluorophenyl)-2hydroxyphenyl,
  2-(3-trifluoromethyl-phenylamino)-phenyl,
  (Z)-5-fluoro-2-methyl-1-(4-methylsulfinylbenzylidene)-1H-inde-3-yl-methyl,
  1-(4-chlorobenzoyl)-5-methoxy-2-methyl-1H-indol-3-yl-methyl,
  1-(3-benzoyl-phenyl)-ethyl,
  2-(2,6-dichlorophenylamino)-benzyl,
  1-[4-(2-thienyl-carbonyl)-phenyl]-ethyl,
when Y is hydrogen,
and is 2-(6-methoxy-2-napthyl)-ethyl when Y is methyl;
$R_1$ is hydroxy, $C_1$-$C_6$ alkoxy, amino, mono-or dialkylamino, in which the alkyl has from 1 to 4 carbon atoms, or an aminoacid radical of the formula:

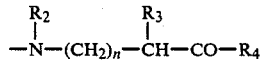

in which
$R_2$ is hydrogen;
$R_3$ is hydrogen, $C_1$-$C_4$ alkyl optionally substituted by SH, $SCH_3$ or by a phenyl optionally substituted by 1 or 2 hydroxy groups;
n is an integer chosen between 0,1 and 2; when n is 0, $R_2$ and $R_3$ together may form a —$(CH_2)_3$— or a —$CH_2$—S—$CH_2$— group;

$R_4$ is hydroxy, $C_1$-$C_6$ alkoxy or a radical of an aminoacid of formula:

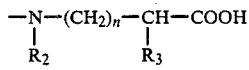

in which $R_2$, $R_3$ and n have the above-stated meanings; and a salt thereof with a pharmaceutically acceptable acid or base.

The compounds of this invention have an antipyretic, anti-inflammatory, mucolytic and analgesic action and furthermore, are active in the treatment of ischemic pathologies and of pathologies caused by the over-production of oxidant radicals.

The preparation of the compounds of this invention is performed by reacting a compound of formula

(II)

wherein R and Y have the above stated meanings, with a compound of

(III)

wherein $R_1$ has the above stated meanings and, when $R_1$ is OH, optionally reacting the so obtained compound of formula

(IV)

with a compound of formula

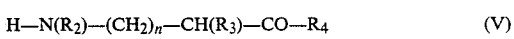

(V)

wherein $R_2$, $R_3$ and $R_4$ have the above stated meanings, and, when desired, adding a pharmaceutically acceptable acid or base.

The reaction of a compound of formula II with a compound of formula III is preferably carried out in an inert atmosphere, in the presence of a base and in a polar solvent.

An example of a suitable base is potassium acetate.

Examples of suitable solvents are water, acetone, alcohols, pyridine and mixtures thereof.

The reaction of a compound of formula IV with a compound of formula V is carried out according to techniques which are known in peptide chemistry, for example in the presence of a suitable condensing agent such as dicyclohexylcarbodiimide and N-hydroxy-benzotriazole.

The compounds of formula V are amino-acids (when $R_4$ is OH), esters of amino acids (when $R_4$ is alkoxy) or dipeptides (when $R_4$ is —$N(R_2)$—$(CH_2)_n$—$CH(R_3)$—COOH) which are known compounds or can be easily prepared according to usual methods, for example by condensing two properly protected amino-acids in the presence of a suitable condensing agent such as dicyclohexylcarbodiimide and N-hydroxy-benzotriazole. The aldehydes of formula II (when Y is H) are known compounds or may be prepared by reducing, according to usual methods, the corresponding carboxylic acids of formula

R—COOH     (VI)

or by oxydation of the corresponding alcohols of formula

R—CH$_2$OH     (VII)

Suitable methods for preparing the aldehydes of formula II are disclosed by U.S. Pat. No.-3,960,936; DE-2,900,620; JP-8302233 and J. Med. Chem. 16 (2) 176–177, 1973.

The carboxylic acids of formula VI are known compounds which are pharmaceutically useful as antipyretic, anti-inflammatory and analgesic agents.

They are known by the following common names:
Ibuprofen (R=1-(4-isobutylphenyl)-ethyl)
Naproxen (R=1-(S)-(6-methoxy-2-napthyl)-ethyl)
Diflunisal (R=5-(2,4-difluorophenyl)-2-hydroxy-phenyl)
Flufenamic acid (R=2-(3-trifluoromethyl-phenylamino)-phenyl)
Sulindac (R=(Z)-5-fluoro-2-methyl-1-(4-methylsulfinylbenzylidene)-1H-iden-3-methyl)
Indomethacin (R=1-(4-chlorobenzoyl)-5-methoxy-2-methyl-1Hindol-3-yl-methyl)
Ketoprofen (R=1-(3-benzoyl-phenyl)-ethyl)
Diclofenac (R=2-(2,6-dichlorophenylamino)-benzyl)
Suprofen (R=1-(4-(2-thienylcarbonyl)-phenyl)-ethyl).

The ketone of formula II (when Y is CH$_3$ and R is 2-(6-methoxy-2-napthyl)-ethyl) is also a drug endowed with an anti-inflammatory and analgesic activity and is known by the name Nabumetone.

The compounds of this invention have various asymmetry centers. Typical asymmetry centers are the carbon atoms in 2- and 4-position of the thiazolidine ring and the carbon atom of the R substituent which is in alpha position to the thiazolidine ring when R is a radical selected from
1-(4-isobutylphenyl)-ethyl,
1-(6-methoxy-2-napthyl)-ethyl,
1-(3-benzoyl-phenyl)-ethyl,
1-(4-(2-thienylcarbonyl)-phenyl)-ethyl.

Choosing appropriately the compounds of formula II and III it is possible to prepare the compounds of formula I having the desired optical isomerism.

For example, starting from (R)-cysteine, the compounds of the formula I are obtained in which the carbon atom in 4-position of the thiazolidine ring has (R) configuration.

Likewise, starting from the aldehydes of formula II in which the carbon atom in alpha position to the carbonyl group has configuration (R) or (S), the compounds of formula I are obtained in which the carbon atom in alpha to the 2-position of the thiazolidine ring has the configuration (R) or respectively (S).

Starting, for example, from an aldehyde of formula

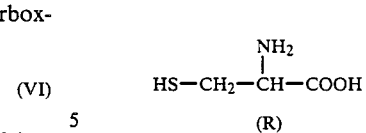

(S)

and from (R)-cysteine

(R)

the corresponding compound of formula

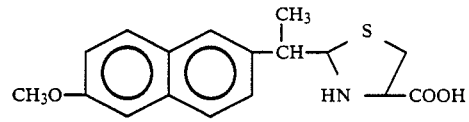

is obtained.

When desired, the diasteroisomeric epimers at the carbon atom in 2-position of the thiazolidine ring may be separated according to conventional techniques, for example, by fractional crystallization or chromatography.

Therefore, this invention provides the compounds of formula I both as a mixture of stereoisomers and as separate isomers prepared either by synthesis or optical separation.

The pharmaceutically acceptable salts of the compounds of formula I can be prepared according to usual methods.

Salts with acids are obtained owing to the nitrogen atom of the thiazolidine ring and, when present, of the amino groups of the susbtituent $R_1$.

Examples of useful acids for preparing salts according to this invention are the pharmaceutically acceptable aliphatic and mineral acids.

In turn, the salts with bases are obtained owing to the carboxy group at 4-position in the thiazolidine ring (when $R_1$ is OH) or, when present, to the carboxy groups of the substituent $R_1$.

Typical examples of compounds according to this invention are the salts of alkali and earth-alkyline metals such as Na, K, Ca and Mg, and of organic bases such as 2-amino-ethanol, trihydroxymethyl-amino-methane, glucosamine, lysine and arginine.

The compounds of this invention are endowed with valuable pharmaceutical properties.

Some of the tests used and the most significant results are shown in example 18.

Compared with the acids of formula VI, the compounds of this invention show a profile of antipyretic, anti-inflammatory and analgesic activity similar in terms of quality and quantity.

However, a salient difference from the said acids is typified by the gastric tolerability which is a serious problem for many acids of formula VI but which is very low and negligible for the compounds of this invention.

The tests for ulcerogenic activity are shown in example 19.

Furthermore, the compounds of this invention proved to be active as mucolytics and in the treatment of ischemic and reperfusion syndromes (M. Bernier et al., Circulation Research, 58, 331–340, 1986) concerning various tissues and parenchymas (for example, by preventing reperfusion and reinfarction arrhythmias) and in the treatment of parenchymal alterations due to an over-production of oxidant radicals owing to endogenous and exogenous factors.

Activity tests for protection against alterations from endotoxin in the rat and from paraquat in the mouse are shown in example 20.

The preventing action on GSH depletion is shown in example 22.

The additional capability of the compounds of this invention in preventing reperfusion arrhythmias in post-infarctual and reinfarctual syndromes proved to be a salient and innovative property.

Once the patient has overcome the acute infarct stage, during reperfusion, aided and abetted by spontaneous thrombolysis or pharmaceutically, or by by-pass operations, he runs serious risks of arrhythmia (ectopic beats, tachycardias and ventricular fibrillation) which in many cases can be lethal.

The compounds of this invention, in tests carried out in the rate (example 21), proved to be very effective in preventing such arrythmias.

Since the compounds of this invention are well tolerated both orally and intravenously, they can be used in human therapy as anti-pyretic, anti-inflammatory, mucolytic and analgesic drugs but above all as drugs suitable for preventing oxidative attacks and reperfusion injuries in the post-infarction and post-ischemia syndromes as well as injuries from oxidant radicals affecting lungs, brain and intestine.

The compounds of this invention can be administered by oral or rectal route at doses of between 200 and 4000 mg/day and by intravenous route at doses of between 100 and 2000 mg/day.

For therapeutical use the compounds of this invention are preferably incorporated into pharmaceutical dosage forms suitable for the desired administration route, such as tablets, pills, capsules, grains, suppositories, solutions, suspensions and lyophilized compositions.

Such pharmaceutical forms are prepared according to conventional techniques and contain a compound of this invention together with solid or liquid pharmaceutical excipients and additives such as, stabilizers, salts for regulating the osmotic pressure, buffers, sweetening and colouring agents suitable for pharmaceutical use.

Particularly useful in preventing reinfarction are also slow-release forms for oral use which are prepared according to conventional techniques.

With the aim of illustrating this invention furthermore, without, however limiting it, the following examples are given.

The $^1$H-NMR spectra and the elemental analysis of the following compounds are consistent with the expected structure.

PREPARATION OF ALDEHYDES

(A) (2RS)-2-(4-isobutylphenyl)-propanal (2RS)-2-(4-isobutylphenyl)-propanoic acid (50 g) is refluxed for 4 hours in a solution of benzene (50 ml) and thionyl chloride (35 ml).

Evaporation of the solvent and non-reacted thionyl chloride leaves a pale green oil (57 g).

An aliquot of the so obtained (2RS)-2-(4-isobutylphenyl)-propanoyl chloride (44.8 g; 0.199 moles) is dissolved in acetone (200 ml); this solution is added dropwise to a suspension of triphenyl phosphine (112 g; 0.427 moles) and bistriphenyl phosphine cupper boron hydride (128 g; 0.212 moles) in acetone (600 ml) kept under stirring at 20° C.

When the addition is over, the reaction mixture is kept under stirring at room temperature for 3 hours. The mixture is filtered and the filtrate is evaporated to dryness under reduced pressure.

The residue is taken up, filtered and again evaporated to dryness under reduced pressure using, sequentially, ethyl ether, chloroform added with cupreous chloride, and ethyl ether.

A yellow oil (47 g) is so obtained, which is purified by chromatography on silica gel (eluent, petroleum ether/ethyl acetate 95:5).

(B) (2R)-2-(4-isobutylphenyl)-propanal (2R)-2-(4-isobutylphenyl)-propanoic acid (41.7 g) is added to benzene (40 ml) and thionyl chloride (29.3 ml). This solution is refluxed for 4 hours. In vacuo evaporation of benzene and of non-reacted thionyl chloride leaves a residue which is taken up many times with benzene followed by evaporation in order to completly remove thionyl chloride. (2R)-2-(4-isobutylphenyl)-propanoyl chloride is so obtained as a colourless oil; yield, 45.8 g.

An aliquot of this chloride (24.5 g; 0.109 moles) is added dropwise to methyl alcohol (100 ml) under stirring at 10° C. This mixture is allowed to stand at room temperature for 48 hours and then is evaporated to dryness. The residue is taken up with ethyl ether and washed with a 5% aqueous solution of sodium bicarbonate.

The ethereal solution is dried and evaporated to dryness.

Methyl (2R)-2-(4-isobutylphenyl)-propanoare is so obtained. Yield, 23.8 g.

An aliquot of this ester (23.5 g; 0.106 moles) is dissolved in anhydrous ethyl alcohol (150 ml).

To this solution, sodium hydride (5.2 g; 0.138 moles) and calcium chloride are added portionwise while keeping the reaction mixture under stirring at −20° C. and in nitrogen atmosphere. This reaction mixture is filtered to discharge the inorganic salt and the filtrate is evaporated to dryness under reduced pressure.

The oily residue is dissolved in ethyl ether and this solution is washed with water till neutral.

The organic phase is dried on sodium sulfate and then evaporated to dryness.

(2R)-2-(4-isobutylphenyl)-propane-1-ol (19.5 g; 95.7%) is so obtained.

An aliquot of this alcohol (18 g; 0.094 moles) is dissolved in methylene chloride (270 ml).

This solution is shaked for 10 minutes in a separatory funnel together with a 3M solution of sulfuric acid containing sodium bichromate dihydrate (8.48 g; 0.028 moles) and tetrabutylammonium acid sulfate (3.17 g; 0.009 moles).

The organic phase is separated, washed, dried on sodium sulfate and evaporated to dryness under reduced pressure.

The desired aldehyde is so obtained as a green oil. Yield, 17.54 g.

(C) (2S)-2-(4-isobutylphenyl)-propanal (2S)-2-(4-isobutylphenyl)-propanoic acid (18 g) is dissolved in an 11 N solution of hydrochloric acid in methyl alcohol (100 ml) and is allowed to stand at room temperature. After 16 hours, the mixture is evaporated under reduced pressure. The residue is taken up with ethyl ether and washed with a 5% aqueous solution of sodium bicarbonate. The organic phase is dried on sodium sulfate and the solvent is removed under reduced pressure.

Methyl (2S)-2-(4-isobutylphenyl)-propanoate is so obtained (Yield, 19.2 g; 100%) as an oil.

This ester is reduced like methyl (2R)-2-(4-isobutylphenyl)-propanoate (see point B above) except that the ethanolic suspension is poured into ice and water, is made acid to ph 3 with hydrochloric acid and extracted with ethyl ether.

Reduction of methyl (2S)-2-(4-isobutylphenyl)-propanoate (19 g; 0.086 mmoles) with sodium boron hydride (3.4 g) and calcium chloride (10 g; 0.09 moles) yields a crude compound (16.65 g) which is purified by chromatography on silica gel (eluent, methylene chloride with gradient of ethyl acetate) (2S)-2-(4-isobutylphenyl)-propane-1-ol is so obtained. Yield, 14.4 g (87%).

Dimethyl sulfoxyde (1.67 ml; 23.5 moles) and methylene chloride (2 ml) are added dropwise to a solution of oxalyl chloride (1.4 g; 11.1 moles) in methylene chloride (15 ml) kept under stirring at −65° C.

After 5 minutes a solution of the above alcohol (2 g; 10.4 mmoles) in methylene chloride (8 ml) is added while maintaining the temperature at −65° C.

After further 5 minutes, triethyl amine (3 ml; 20.8 moles) is added dropwise while the temperature is maintained at −65° C. and pH is maintained below 7.

The mixture is allowed to warm to room temperature, water is added and the organic phase is separated. After drying on sodium sulfate and removal of the solvent under reduced pressure, the desired aldehyde is obtained as a colourless oil. Yield, 1.9 (95%).

(D) (2S)-2-(6-methoxy-2-naphthyl)-propanal

Thionyl chloride (63 ml) is added to a suspension of (2S)-2-(6-methoxy-2-napthyl)-propanoic acid (25 g; 0.108 moles) in methylene chloride (250 ml) at room temperature and under stirring.

The mixture is refluxed for 4 hours and a half. Afterwards, the solvent and the excess of thionyl chloride are removed by distillation. The residue is taken up many times with benzene and evaporated to dryness.

(2S)-2-(6-methoxy-2-napthyl)-propanoyl chloride (29 g) is so obtained as a yellow solid.

An aliquot of this acid chloride (21.6 g; 0.093 moles), bistriphenyl phosphine copper boron hydride (60 g; 0.099 moles) and triphenyl phosphine (52.3 g; 0.199 moles) in acetone (330 ml) are reacted as described above in relation to (2RS)-2-(4-isobutylphenyl)-propanal (see point A above).

An oil (23 g) is so obtained which is dissolved in ethyl ether and treated with a 40% aqueous solution of sodium metabisulfite and with ethyl alcohol (30 ml).

The mixture is kept under stirring at room temperature for 4 hours, the solid is collected by filtration, washed with water, acetone and lastly with ethyl ether. The solid (14.7 g) is suspended in a 5% solution of sodium bicarbonate and is stirred for 10 minutes at room temperature.

This mixture is extracted with ethyl ether. The ethereal extracts are dried and the solvent is removed by evaporation.

The desired aldehyde is so obtained as an oil. Yield, 8.2 g (41%).

(E) (2RS)-2-(3-benzoylphenyl)-propanal

Methyl (2RS)-2-(3-benzoylphenyl)-propanoate (52 g) is obtained from the corresponding acid (50 g; 0.19 moles) as described above in relation to methyl (2R)-2-(4-isobutylphenyl)-propanoate (see point B above).

An aliquot (50 g; 0.19 moles) of the so obtained aster is added portionwise to a suspension of lithium aluminum hydride (8.77 g; 0.23 moles) in tetrahydrofuran (800 ml) while stirring at 0° C. When the addition is over, the mixture is allowed to warm to room temperature. To this mixture, ethyl acetate (200 ml), a saturate solution of sodium sulfate (200 ml) and a 5% solution (400 ml) of sulfuric acid are added under stirring.

The organic phase is separated and the aqueous phase is washed with ethyl acetate (400 ml). The combined organic extracts are dried on sodium sulfate and the solvent is removed under reduced pressure.

(RS)-2-[4-(α-hydroxy-benzyl-phenyl)]-propane-1-ol (48 g) is so obtained as a colourless oil.

An aliquot (25 g; 0.1 moles) of this alcohol is reacted with dimethyl sulfoxyde (35 ml; 0.49 moles), oxalyl chloride (19 ml; 0.22 moles) and triethyl amine (62.5 ml; 0.45 moles) as described for (2S)-2-(4-isobutylphenyl)-propanal (see point C above).

The desired aldehyde is so obtained as an oil. Yield, 25.37 g.

(F) 2-[(3-trifluoromethyl)-phenylamine]-benzaldehyde

2-[(3-trifluoromethyl)-phenylamino]-benzoic acid (50 g; 0.177 moles), thionyl chloride (50 ml; 0.688 moles) and benzene (50 ml) are stirred for 16 hours at room temperature. Benzene and non-reacted thionyl chloride are removed by distillation. The residue is taken up with benzene which is then removed by distillation; this step is repeated many times.

2-[(3-trifluoromethyl)-phenylamino]-benzoyl chloride (56.2 g) is so obtained as a red solid.

An aliquot (53 g; 0.177 moles) of this chloride is dissolved in anhydrous tetrahydrofuran and cooled to −85° C.

To this solution, lithium triterburyloxy aluminum hydride (50.8 g; 0.2 moles) in anhydrous tetrahydrofuran (115 ml) is added dropwise.

When the addition is over, the mixture is stirred at −80° C. for 2 hours and then is poured into water and ice (500 ml) containing 5% hydrochloric acid (50 ml). This mixture is extracted with ethyl ether. The ethereal extracts are washed with water and with a 5% solution of sodium bicarbonate, dried and evaporated.

The residue is purified by chromatography on silica gel (eluent, petroleum ether with gradient of methylene chloride).

The desired aldehyde is so obtained as a yellow solid. Yield, 9.46 g (20%).

(G) 5-(2,4-difluorophenyl)-salicylaldehyde

To a solution of 5-(2,4-difluorophenyl)-salicylic acid (50 g; 0.2 moles) in methyl alcohol (500 ml), conc. sulfuric acid (15 ml) is added dropwise under stirring at room temperature.

The mixture is refluxed. After 20 hours the mixture is cooled and concentrated under reduced pressure. The residue is taken up with ethyl ether, washed many times with water and once with a 5% solution of sodium bicarbonate.

The organic phase is dried on sodium sulfate and the solvent is removed under reduced pressure.

Methyl 5-(2,4-difluorophenyl)-salicylate is so obtained as a solid (54.5 g) which is crystallized from methyl alcohol (500 ml). Yield, 47 g; m.p.=101°–102° C.

This ester (47 g) is reduced with lithium aluminum hydride (7.9 g; 0.2 moles) as described for (2RS)-2-[4-(α-hydroxybenzyl-phenyl)]-propane-1-ol (see point E above).

5-(2,4-difluorophenyl)-salicyl alcohol (41.72 g) is so obtained, which is crystallized from ethyl acetate (200 ml) and then from hexane (180 ml).

Yield, 36.9 g (87.7%); m.p. = 143°–145° C.

An aliquot of this alcohol (2.4 g; 0.01 moles) is dissolved at room temperature in 1N sodium hydroxide (10 ml) and tetrahydrofuran (5ml).

To this solution, lead nitrate (0.5 g) in water (5 ml) and then 10% platinum on carbon (240 mg) are added. This mixture is stirred at 45° C. for 30 hours.

The mixture is cooled to room temperature, the catalyst is removed by filtration, the solution is made acid (Congo Red) with 10% hydrochloric acid and extracted with ethyl ether. The organic layer is dried on sodium sulfate and the solvent is removed by evaporation under reduced pressure.

The desired aldehyde is so obtained as a white solid. Yield, 1.9 g (81%).

(H)
2-[1-(4-chlorobenzoyl)-2-methyl-5-methoxy-indol-3-yl]-acetaldehyde

In a suspension of 2-[1-chlorobenzoyl)-2-methyl-5-methoxy-indol-3-yl]-acetic acid (50 g; 0.139 moles) in carbon tetrachloride (280 ml), thionyl chloride (20 ml; 0.278 moles) and then dimethylformamide (4ml) are added dropwise while stirring at room temperature.

When the addition is over, the solution is kept under stirring for 15 minutes. The solvent is removed under reduced pressure. The residue is taken up with benzene which is then removed; this step is repeated many times.

2-[1-(4-chlorobenzoyl)-2-methyl-5-methoxy-indol-3-yl]-acetyl chloride is so obtained. Yield, 53.54.

An aliquot (20 g; 0.053 moles) of this chloride is treated as described for 2-[(3-trifluoromethyl)-phenylamino]-benzaldehyde (see point F above). Purification is carried out by chromatography on silica gel (eluent, petroleum ether ethyl acetate, 90:10).

The desired aldehyde is so obtained as an amorphous solid. Yield, 5 g.

EXAMPLE 1

4R)-2-[1-(4-isobutylphenyl)-ethyl]-thiazolidine-4-carboxylic acid (Compound No. 1)

To a suspension of (R)-cysteine hydrochloride (7.88 g; 0.05 moles) and potassium acetate (4.9 g; 0.05 moles) in a mixture of water and ethanol (150 ml; 1:1 v/v) previously deoxygenated by a stream of nitrogen, a solution of (2RS)-2-(4-isobutylphenyl)-propanal (10 g; 0.052 moles) in ethanol (10 ml) is added dropwise while stirring at room temperature.

In a short time the almost complete dissolution of cysteine is observed, meanwhile a precipitate begins to form.

After 20 minutes the precipitate is filtered, washed with plenty of water and dried, obtaining a crude product (13.27 g) which is crystallized from methanol (250 ml) to produce the desired product in a pure form (9 g; 55.5% yield). m.p. = 160°–163° C. (dec.); $[\alpha]_D^{20} = -63.4°$ (c=1, DMF).

EXAMPLE 2

Methyl (4R)-2-[1-(4-isobutylphenyl)-ethyl]-thiazolidine-4-carboxylate hydrochloride. (Compound No. 2)

To a solution of (R)-cysteine methyl ester hydrochloride (8.12 g; 47.3 mmoles) and potassium acetate (5 g; 51 mmoles) in a mixture of water (45 ml) and methanol (35 ml) previously deoxygenated by a stream of nitrogen, a solution of (2RS)-2-(4-isobutyl-phenyl)-propanal (9 g; 0.0473 moles) in ethanol (10 ml) is added dropwise under stirring at room temperature.

After 30 minutes an oil separates which is extracted with ethyl ether.

The separated extract is anhydrified on sodium sulfate and evaporated to dryness obtaining a colourless oil (9.35 g) which is dissolved into ethyl ether and treated with gaseous hydrochloric acid. By addition of pentane a white crystalline solid (12.36 g) melting at 140°–145° C. precipitates, which is recrystallized from ethyl acetate and then from acetonitrile obtaining the desired product in a pure form (6.5 g; 39.7% yield) m.p. = 148°–152° C. (dec.)

EXAMPLE 3

Hexyl (4R)-2-[1-(4-isobutylphenyl)-ethyl]-thiazolidine-4-carboxylate hydrochloride (Compound No. 3)

To a solution of (R)-cysteine hexyl ester (7 g; 28.9 mmoles) and potassium acetate (3.06 g; 31.2 mmoles) in a mixture of water and ethanol (80 ml; 1:1 v/v) previously deoxygened by a stream of nitrogen, a solution of (2RS)-2-(4-isobutylphenyl)-propanal (5.5 g; 0.0289 moles) in ethanol (10 ml) is added dropwise while stirring at room temperature.

The reaction product is extracted with ethyl ether obtaining, after anhydrification and solvent evaporation, an oil (11 g) which is purified by chromatography on silica gel (eluent, petroleum ether: ethyl acetate, 87:13).

An oil (8 g) is obtained which is dissolved in ethyl ether and treated with gaseous hydrochloric acid.

The resulting mixture is taken to dryness and the residual oil, that after some days solidifies and crystallizes, is recovered by pentane and filtered obtaining the desired product as a white crystalline solid (2.37 g; 19.76% yield); m.p. = 115°–117° C. (dec.); $[\alpha]_D^{20} = -47.2°$ (c=1, DMF).

EXAMPLE 4

Operating in a way similar to that described in the preceeding examples, the following compounds have been prepared:

Compound No. 4

(4R)-2-[(1R)-1-(4-isobutylphenyl)-ethyl]-thiazolidine-4-carboxylic acid m. p. = 170°–172° C. (dec.) (methanol; $[\alpha]_D^{20} = -36.1°$ (c=1, DMF)

Compound No. 5

Methyl (4R)-2-[(1R)-1-(4-isobutylphenyl)-ethyl]-thiazolidine-4-carboxylate hydrochloride m.p. = 150°–154° C. (dec.) (acetonitrile: isopropyl ether 1:1) $[\alpha]_D^{20} = -42.4°$ (c=1, DMF).

Compound No. 6

(4R)-2-[(1S)-1-(4-isobutylphenyl)-ethyl]-thiazolidine-4-carboxylic acid m. p. = 138°–140° C. (dec.) (methanol); $[\alpha]_D^{20} = -97.0°$ (c=1, DMF).

EXAMPLE 5

Preparation of
(4R)-2-[(1S)-1-(6-methoxy-2-napthyl)-ethyl]-thiazolidine-4-carboxylic acid (Compound No. 7)

To a solution of (R)-cysteine hydrochloride (5.94 g; 0.0376 moles) and potassium acetate (3.69 g; 0.0376 moles) in a mixture of water and acetone (100 ml; 1:1 v/v), a solution of (2S)-2-(6-methoxy-2-napthyl)-propanal (8.2 g; 0.0383 moles) in acetone (50 ml) is added dropwise while stirring at room temperature.

Slowly a precipitate is formed that after one hour at room temperature is filtered and washed with a mixture of water and acetone (1:1 v/v) first and then with acetone alone.

The desired product is obtained as a white crystalline solid (6 g; 50.3% yield). m.p.=184°–186° C. (dec.); $[\alpha]_D^{20} = -69.8°$ (c=1, DMF).

EXAMPLE 6

(4R)-2-[1-(3-benzoylphenyl)-ethyl]-thiazolidine-4-carboxylic acid hydrochloride (Compound No. 8)

To a solution of (R)-cysteine hydrochloride (15 g; 0.095 moles) and potassium acetate (9.3 g; 0.095 moles) in water and acetone (270 ml; 1:1 v/v), 2-(3-benzoylphenyl)-propanal (16 g; 0.066 moles) is added dropwise at room temperature.

At the end of the addition the solution is kept under stirring at room temperature for 20 hours, afterwards the solvent is evaporated under reduced pressure.

The oily residue is purified by chromatography on 230–400 mesh silica gel (eluent, methylene chloride/methanol/acetic acid, 95:5:1) obtaining a dense oil (19 g).

This oil is dissolved in ethyl acetate (600 ml) and treated with 20 ml of 3N hydrochloric acid in ethyl ether.

When adding ethyl ether (600 ml) the desire product precipitates as a white crystalline solid, which is separated by filtration (10.7 g; 43% yield). m.p.=123°–126° C.; $[\alpha]_D^{20} = -47.4°$ (c=1, DMF).

EXAMPLE 7

Methyl
N-[2-[1-(4-isobutylphenyl)-ethyl]-thiazolidine-4(R)-carbonyl]-gylcinate (Compound No. 10)

To a solution of (4R)-2-(4-isobutylphenyl)-ethyl]-thiazolidine-4-carboxylic acid (Compound No. 1, Example 1) (10 g; 0.034 moles) and tetramethylguanidine (4.3 ml; 0.034 moles) in dimethylformamide (DMF) (100 ml) kept under stirring at 0° C., a solution of diterburylcarbonate (8.16 g; 0.037 moles) in DMF (10 ml) is added dropwise.

The mixture is allowed to warm to room temperature and after 45 minutes the solvent is removed by evaporation under reduced pressure.

The residue is taken up with water and the aqueous solution is washed with ethyl acetate and then acidified with citric acid to pH 3.

By subsequent extraction with ethyl acetate, anydrification on Na$_2$SO$_4$ and solvent evaporation under reduced pressure, a solid (10.5 g) is obtained consisting of (4R)-2-[1-(4-isobutylphenyl)-ethyl]-N-terbutyloxycarbonyl-thiazolidine-4-carboxylic acid (Compound No. 9).

Compound No. 9 (1 g; 2.54 10$^{-3}$ moles) is dissolved in ethyl acetate (2.5 ml) and N-methyl-morpholine (0.285 ml; 2.54 10$^{-3}$ moles). To the solution cooled to −15° C., isobutyl chloroformate (0.32 ml; 2.54 10$^{-3}$ moles) is added dropwise.

After 5 minutes, methyl glycinate hydrochloride (0.32 g; 2.54 10$^{-3}$ moles) and then N-methyl-morpholine (0.285 ml; 2.54 10$^{-3}$ moles) are added at the same temperature (−15° C.).

To so obtained suspension is kept under stirring for 10 minutes at −15° C. and then for 1 hour at room temperature.

The reaction mixture is diluted with water and the organic phase is separated, washed with a 5% aqueous solution of citric acid, followed by a 5% aqueous solution of NaHCO$_3$, and anhydrified on Na$_2$SO$_4$.

After evaporating the solvent under reduced pressure, an oil is obtained that is chromatografied on silica gel (eluent, dichloromethane: ethyl acetate, 9:1).

A colourless oil is thus obtained (0.91 g) consisting of methyl N-[2-[1-(4-isobutylphenyl)-ethyl]-3-terbutyloxycarbonyl]-thiazolidine-4(R)-carbonyl -glycinate (Compound No. 11). Compound No. 11 (8 g; 17.2 10$^{-3}$ moles) is dissolved at room temperature in a 4N hydrochloric acid solution in diethyl ether (80 ml).

After 1 hour the solution is evaporated under reduced pressure and the residue is taken up with diethyl ether and treated with a 5% NaHCO$_3$ aqueous solution and then with water and is anhydrified on Na$_2$SO$_4$.

Compound No. 10 is isolated as a dense oil after solvent evaporation.

EXAMPLE 8

Methyl N-[2 -[1-(4-isobutylphenyl)-ethyl]-thiazolidine-4(R)-carbonyl]-glycinate hydrochloride (Compound No. 12)

The preparation of compound No. 12 (hydrochloride of Compound No. 10, Example 7) is performed by treating Compound No. 10 in a solution of diethyl ether and diisopropyl ether 1:1 with a stoichiometric amount of hydrochloric acid in a 4N solution of diethyl ether.

Compound No. 12 appears as a hygroscopic white solid. m.p.=70°–73° C. (dec.); $[\alpha]_D^{20} = -69.5°$ (c=1%, EtOH) Mass spectrum (DCI) m/e=365 (M+1)

EXAMPLE 9

N-[2-[1-(4-isobutylphenyl)-ethyl]-thiazolidine-4(R)-carbonyl]-glycine hydrochloride (Compound No. 13).

To a solution of Compound No. 11 (Example 7) (8.7 g; 0.0187 moles) in methanol (60 ml), an 1N sodium hydroxide aqueous solution (16.93 ml) is added at room temperature.

After stirring for 2 hours at room temperature, methanol is removed by evaporation under reduced pressure and the residue is taken up with water. The so obtained solution is washed with diethyl ether and then acidified with citric acid to pH 3.

The solution is extracted with diethyl ether and the combined extracts are made anhydrous on Na$_2$SO$_4$.

By evaporating the solvent under reduced pressure, a solid is obtained (8.13 g) consisting of N-[2-[1-(4-isobutylphenyl)ethyl]-3-terbutyloxycarbonyl-thiazolidine-4-carbonyl]-glycine (Compound No. 14)

Compound No. 14 is dissolved at room temperature in a 4N hydrochloric acid solution in diethyl ether.

After 1 hour the solvent is removed by evaporation under reduced pressure and the residue is treated with heptane.

Compound No. 13 is so obtained as a white, hygroscopic solid. m.p. =90°–93° C. (dec.); $[\alpha]_D^{20} = -32.34°$

EXAMPLE 10

Methyl (4R)-2-[2-(3-trifluoromethyl)-phenylamino]-phenyl-thiazolidine-4-carboxylate hydrochloride (Compound No. 15).

To a solution of R-cysteine methyl ester hydrochloride (3.3 g; 0.048 moles) in pyridine (100 ml), deoxygenated by a stream of nitrogen and kept under stirring at room temperature, 2-[(3-trifluoromethyl)-phenylamino]-benzaldehyde (11.7 g; 0.0044 moles is added.

After stirring for 4 hours at room temperature, the reaction mixture is poured into water (1000 ml) and extracted with diethyl ether.

The combined ethereal extracts are made anhydrous on $Na_2SO_4$ and the solvent is removed by evaporation under reduced pressure.

The residual oil is purified by chromatography on silica gel (eluent, dichloromethane: ethyl acetate, 97:3) obtaining an oil (16 g).

A portion of said oil (4.3 g) is dissolved in isopropyl ether (20 ml). To this solution, kept at room temperature, a 4N hydrochloric acid solution in ethyl ether (3 ml) is added.

A solid separates that is washed with ligroin. Compound No. 15 (4 g) is so obtained as a solid. m.p.=70°–73° C.; $[\alpha]_D^{20} = +153.6°$ (c=1% in DMF)

(4R)-2-[(1S)-1-(6-methoxy-2-napthyl)-ethyl]-thiazolidine-4-carboxylic acid (Compound No. 15/A)

A solution of (2S)-2-(6-methoxy-2-napthyl)-propanal (8.2 g; 38.3 mmoles) in acetone (50 ml) is added dropwise to a solution of (R)-cysteine hydrochloride (5.94 g; 37.6 mmoles) and of potassium acetate (3.69 g; 37.6 mmoles) in 100 ml of water and acetone (1:1 v/v) kept under stirring at room temperature.

A solid precipitates slowly. After 1 hour, the solid is recovered by filtration, washed with a mixture of water and acetone (1:1 v/v) and then with acetone alone.

White, crystalline compound (6 g; 50.3%) m.p.=184°–186° C. (dec.)

(4R)-2-[1-(4-benzolyphenyl)-ethyl]-thiazolidine-4-carboxylic acid hydrochloride (Compound No. 15/B)

A solution of (2RS)-2-(4-benzoylphenyl)-propanal (22.8 g; 0.095 moles) in acetone (165 ml) is added dropwise to a solution of cysteine hydrochloride (15 g; 0.095 moles) and of potassium acetate (9.3 g; 0.095 moles) in 270 ml of water and acetone (1:1 v/v) previously deaerated with nitrogen and kept under stirring at room temperature.

After standing 48 hours at room temperature, the mixture is evaporated to dryness under reduced pressure and the residue is purified by chromatography on silica gel (eluent, methylene chloride/methyl alcohol/acetic acid, 95:5:1).

The so obtained compound (19.1 g) is dissolved in ethyl acetate (600 ml) and treated with 4N ethereal hydrochloric acid (14 ml) at room temperature.

The hydrochloride salt which precipitates is recovered by filtration and dried.

Yield, 10.7 g (42.6%); m.p.=123°–125° C. (dec.)

EXAMPLE 11

(4R)-2-[(1RS)-1-(4-isobutylphenyl)-ethyl]-N-terbutyloxycarbonyl-thiazolidine-4-carboxylic acid (Compound No. 9)

Triethyl amine (27.8 ml; 0.20 moles) is added dropwise to a suspension of Compound No. 1 (58.7 g; 0.20 moles) in dimethyl formamide (500 ml) kept under stirring at 0° C.; to this suspension is added dropwise at 0° C. a solution of diterbutyl dicarbonate (52.4 g; 0.24 moles) in dimethyl formamide (50 ml).

The reaction mixture is allowed to warm to room temperature. After 45 minutes the solvent is removed under reduced pressure at a temperature below 40° C.

The residue is taken up with water and ethyl ether and the aqueous solution is made acid to pH 3 with citric acid. From the separated organic layer, dried on sodium sulfate and evaporated to dryness, a vitreous solid (86 g) is obtained.

(4R)-2-[(1S)-1-(4-isobutylphenyl)-ethyl]-N-terbutyloxycarbonylthiazolidine-4-carboxylic acid (Compound No. 17)

Starting from Compound No. 6 (40 g; 0.136 moles) and operating in a way similar to the preparation of Compound No. 9, an amorphous solid is obtained (48.8 g; yield, 91%).

(4R)-2-[(1R)-1-(4-isobutylphenyl)-ethyl]-N-terbutyloxycarbonylthiazolidine-4-carboxylic acid (Compound No. 18)

Starting from Compound No. 4 (40 g; 0.136 moles) and operating in a way similar to the preparation of Compound No. 9, a vitreous compound is obtained (53.6 g).

EXAMPLE 12

Methyl 2-[(1RS)-1-(4-isobutylphenyl)-ethyl-N0Terbutyloxcarbonyl-thiazolidine-4-carbonyl]-glycinate Compound No. 11)

N-methylmorpholine (7.1 ml; 0.063 moles) and then isobutyl chloroformate (8.6 ml; 0.063 moles) are added dropwise to a solution of Compound 16 (25 g; 0.063 moles) in ethyl acetate (50 ml) kept under stirring at −15° C.

After 5 minutes, methyl glycinate hydrochloride (7.9 g; 0.063 moles) is added portionwise and then N-methylmorpholine (7.1 ml; 0.063 moles) is added dropwise while keeping the temperature at −15° C.

The reaction mixture is allowed to warm to room temperature. After 1 hour and a half a 10% solution (50 ml) of citric acid is added and the organic phase is separated. The latter phase is washed with water, then with a 5% solution of sodium bicarbonate and, finally, with water again. After drying and solvent evaporation, the residue (25 g) is purified by chromatography on silica gel eluting with methylene chloride with gradient of ethyl acetate.

A colourless oil (17.83 g; yield, 61%) is so obtained.

Methyl N-[(4R)-2-[(1RS)-1-(4-isobutylphenyl)-ethyl]-N-terbutyloxycarbonyl-thiazolidine-4-carbonyl]-β-alanate (Compound No. 20)

Compound No. 16 (30 g; 0.076 moles) is reacted with methyl β-alanate (10.63 g; 0.076 moles) in a way similar to the preparation of Compound No. 11. The resulting compound is purified by chromatography on silica gel eluting with methylene chloride with gradient of methyl alcohol. An amorphous solid is so obtained (16.5 g; Yield, 45%).

Methyl
N-[(4R)-2-[(1RS)-1-(4-isobutylphenyl)-ethyl]-N-ter-butyloxycarbonyl-thiazolidine-4-carbonyl]-L-alanate (Compound No. 21)

Compound No. 16 (23.7 g; 0.060 moles) and methyl L-alanate hydrochloride (8.4 g; 0.060 moles) are reacted in a way similar to the preparation of Compound No. 11.

The crude is purified by chromatography on silica gel eluting with methylene chloride with gradient of methyl alcohol.

An amorphous solid is so obtained (13.8 g; yield 48%).

EXAMPLE 13

Ethyl
N-[(4R)-2-[(1S)-1-(4-isobutylphenyl)-ethyl]-N-ter-butyloxycarbonyl-thiazolidine-4-carbonyl]-β-alanate (Compound No. 22)

N-methylmorpholine (13.3 ml; 0.121 moles) and then isobutyl chloroformate (16.8 ml; 0.128 moles) are added to a solution of Compound No. 17 (47.5 g; 0.121 moles) in ethyl acetate (250 ml) kept at −15° C.

After 10 minutes, a solution of ethyl β-alanate hydrochloride (18.54 g; 0.121 moles) and of N-methyl morpholine (13.3 ml; 0.121 moles) in ethyl acetate (150 ml) and dimethylformamide (40 ml) is added, while maintaining the temperature at −15° C.

The reaction mixture is allowed to warm to room temperature and after 30 minutes a 10% solution of citric acid is added. The aqueous layer is separated, washed with water, then with a 5% solution of sodium bicarbonate and, finally, with water again.

After drying and evaporation of the solvent, the residue is purified by chromatography on silica gel eluting with methylene chloride.

An oily compound is obtained (51.5 g; Yield, 86.6%)

Ethyl
N-[(4R)-2-[(1R)-1-(4-isobutylphenyl)-ethyl]-N-ter-butyloxycarbonyl-thiazolidine-4-carbonyl]-β-alanate (Compound No. 23).

Starting from Compound No. 18 (53 g; 0.134 moles) and operating in a way similar to the preparation of Compound No. 22, the desired compound is obtained (25 g; Yield, 37.8%).

EXAMPLE 14

N-[(4R)-2-[(1RS)-1-(4-isobutylphenyl)-ethyl]-N-ter-butyloxycarbonyl]-thiazolidine-4-carbonyl-glycine (Compound No. 14)

To a solution of Compound No. 11 (8.7 g; 18.7 mmoles) in methyl alcohol (60 ml) kept under stirring at room temperature, an 1N solution of sodium hydroxide (19.6 ml) is added dropwise.

After 2 hours at room temperature, the mixture is evaporated to dryness under reduced pressure and the residue is taken up with water and ethyl ether.

After separation of the organic layer, the aqueous phase is made acid to pH 3 with an aqueous solution of citric acid and extracted with ethyl ether.

The ethereal phase is dried on sodium sulfate and evaporated under reduced pressure. An amorphous solid is obtained (8.13 g; Yield, 96%).

N-[(4R)-2-[(1RS)-1-(4-isobutylphenyl)-ethyl]-N-ter-butyloxycarbonyl-thiazolidine-4-carbonyl]-β-alanine (Compound No. 25)

Starting from Compound No. 20 (6 g; 0.0125 moles) and operating in a way similar to the preparation of Compound No. 14, a vitreous solid is obtained (5.6 g).

N-[(4R)-2-[(1RS)-1-(4-isobutylphenyl)-ethyl]-N-ter-butyloxycarbonyl-thiazolidine-4-carbonyl]-L-alanine (Compound No. 26)

Starting from Compound No. 21 (7 g; 0.0146 moles) and operating in a way similar to the preparation of Compound No. 14, a vitreous solid is obtained (6.9 g).

N-[(4R)-2-[(1S)-1-(4-isobutylphenyl)-ethyl]-N-ter-butyloxycarbonyl-thiazolidine-4-carbonyl]-β-alanine (Compound No. 27)

Starting from Compound No. 22 (17.5 g) and operating in a way similar to the preparation of Compound No. 14, an amorphous solid is obtained (15.7 g; yield, 92.5%).

N-[(4R)-2-[(1R)-1-(4-isobutylphenyl)-ethyl]-N-ter-butyloxycarbonyl-thiazolidine-4-carbonyl]-β-alanine (Compound No. 28)

Starting from Compound No. 23 (13.8 g; 0.028 moles) and operating in a way similar to the preparation of Compound No. 14, an oily compound is obtained (12 g; yield, 92%).

EXAMPLE 15

Methyl
N-[(4R)-2-[(1RS)-1-(4-isobutylphenyl)-ethyl]thiazolidine-4-carbonyl]-glycinate hydrochloride (Compound No. 12)

Compound No. 11 (8 g) is dissolved in 4N ethereal hydrochloric acid (80 ml) at room temperature.

The reaction mixture is kept under stirring at room temperature for 1 hour, then is evaporated to dryness under reduced pressure and the residue is taken up with petroleum ether. The so obtained hydrochloride salt is filtered and dried. Yield, 5.24 g (76%); m.p. 70°–73° C.

N-[(4R)-2-[(1RS)-1-(4-isobutylphenyl)-ethyl]-thiazolidine-4-carbonyl]-glycine hydrochloride (Compound No. 13)

Compound No. 13 is prepared from Compound No. 14 (8 g; 1.77 mmoles) in a way similar to the preparation of Compound No. 12 except that the residue is taken up with heptane in lieu of petroleum ether. Yield, 6.45 g (94%). m.p.=90°–93° C.

Methyl
N-[(4R)-2-[(1RS)-1-(4-isobutylphenyl)-ethyl]thiazolidine-4-carbonyl]- -alanate hydrochloride (Compound No. 31)

Compound No. 31 is prepared from Compound No. 20 (8 g; 0.0167 moles) in a way similar to the preparation of Compound No. 12.

Yield, 5.7 g (82%); m.p. 95°–102° C.

N-[(4R)-2-[(1RS)-1-(4-isobutylphenyl)-ethyl]-thiazolidine-4-carbonyl]β-alanine hydrochloride (Compound No. 32)

Compound No. 32 is prepared from Compound No. 25 (5.6 g; 0.012 moles) in a way similar to the preparation of Compound No. 12 except that the residue is taken up with isopropyl ether.

Yield, 4.56 g (95%)

Methyl N-[(4R)-2-[(1RS)-1-(4-isobutylphenyl)-ethyl]thiazolidine-4-carbonyl]-L-alanate hydrochloride (Compound No. 33)

Compound No. 33 is prepared from Compound No. 21 (6.5 g; 0.0135 moles) in a way similar to the preparation of Compound No. 12.

Yield, 4.9 g (87.5%); m.p. = 85°–93° C.

N-[(4R)-2-[(1RS)-1-(4-isobutylphenyl)-ethyl]-thiazolidine-4-carbonyl]-L-alanine hydrochloride (Compound No. 34)

Compound No. 34 is prepared from Compound No. 26 (6.6 g; 0.0143 moles) in a way similar to the preparation of Compound No. 12 except that the residue is taken up with ethyl ether.

Yield, 4.53 g (79%).

Ethyl N-[(4R)-2-[(1R)-1-(4-isobutylphenyl)-ethyl]-thiazolidine-4carbonyl]-β-alanate hydrochloride (Compound No. 37)

Compound No. 37 is prepared like Compound No. 12 starting from Compound No. 23 (11 g; 0.022 moles).

Yield, 7.5 g (79.4%); m.p. 58°–63° C.

EXAMPLE 16

Ethyl N-[(4R)-2-[(1S)-1-(4-isobutylphenyl)-ethyl]-thiazolidine-4-carbonyl]-β-alanate hydrochloride (Compound No. 35)

Compound No. 22 (32 g; 0.065 moles) is dissolved in ethyl ether (50 ml). To this solution, 4N ethereal hydrochloric acid (300 ml) is added at room temperature.

After 2 hours a white, crystalline product precipitates. The mixture is allowed to stand at room temperature for further 4 hours and then is evaporated to dryness under reduced pressure. The solid residue is suspended in ethyl ether (100 ml) and filtered. The solid is dried.

Yield, 24 g (86%); m.p. = 148°–151° C.

EXAMPLE 17

N-[(4R)-2-[(1S)-1-(4-isobutylphenyl)-ethyl]-thiazolidine-4-carbonyl]-β-alanine hydrochloride (Compound No. 36).

Compound No. 27 (15.5 g; 0.032 moles) is dissolved in ethyl ether (15 ml). To this solution, 4N ethereal hydrochloric acid (150 ml) is added.

The reaction mixture is kept at room temperature for 5 hours; afterwards is evaporated to dryness under reduced pressure.

The solid residue is suspended in isopropyl ether (100 ml) and kept under stirring at room temperature for 24 hours.

The solid is separated by filtration and dried.

Yield, 10 g (77%); m.p. = 80°–85° C.

N-[(4R)-2-[(1R)-1-(4-isobutylphenyl)-ethyl]-thiazolidine-4-carbonyl]-β-alanine hydrochloride (Compound No. 38)

Compound No. 38 is prepared like Compound No. 36 starting from Compound No. 28 (11 g; 0.023 moles).

Yield, 8.6 g (93.2%).

EXAMPLE 18

The analgesic, anti-inflammatory and antipyretic activity of the compounds of this invention has been evaluated by the following tests:

Analgesic activity: stretching from acetic acid in the mouse.

The evaluation has been carried out according to Koster et al. (Fed. Proc., 18, 412, 1953).

The compounds under test have been administered orally 30 min. before acetic acid.

The evaluation of the possible writhing inhibiting effect has been made for 20 min. after injection of acetic acid.

Compounds No. 1 and 5 have shown an activity (expressed as $ED_{50}$) substantially similar to that of Ibuprofen.

Anti-inflammatory activity: oedema from carragenine in the rat.

The evaluation has been carried out according to C. A. Winter et al. (Proc. Soc. Exp. Biol. N.Y., 111, 544, 1962).

The limb volumes have been measured 2, 3 and 5 hours after the treatment. The tested compounds have been administered 30 min. before underplantar injection of carragenine.

Compounds 4 and 6 have shown, after oral administration, an activity (expressed as $ED_{50}$) substantially similar to that of Ibuprofen.

Antipyretic activity: hypertermia from yeast in the rat.

The evaluation has been carried out according to L. Joulon et al. (Arzn. - Forsch./Drug Res., 8, 1198, 1969).

The activity has been calculated 1 hour after peritoneal administration and 2 hours after oral administration.

Compounds Nos 1, 2, 4 and 6 have shown, after oral administration, an activity substantially similar to that of the Ibuprofen.

EXAMPLE 19

The gastric lesivity of the compounds of this invention has been evaluated by administering orally 0.1 mmoles/kg of test compound, 10 times during a 48 hours period.

The data reported in the following table represent the mean values varying on a scale from 1 to 100 (X=see table) depending on the degree of tissue lesions observed.

TABLE

Ulcerogenic activity: repeated administrations (0.1 mmoles/kg, p.o. 10 times) in the rat on an empty stomach.

| Treatment (Compound No.) | No. of animals | Score X | +ES |
|---|---|---|---|
| Controls | 14 | 1.4 | +0.9 |
| 1 | 13 | 18.4 | +5.6 |
| 6 | 14 | 9.3 | +4.1 |
| 2 | 14 | 16.4 | +3.5 |
| 5 | 6 | | 0 |
| 7 | 14 | 24.2 | +5.6 |
| Ibuprofen | 14 | 60.0 | +6.7 |

EXAMPLE 20

The activity of the compounds of formula I in the prevention and cure of pathologies from overproduction of oxidant radicals has been evaluated by the following tests.

Influence on death induced by endotoxin (lipopolysaccharide β, salmonella enteritis) in the rat.

The tests have been carried out according to W. L. Wise et al. (J. Pharm. Exp. Ther., 215, 160, 1980).

Endotoxin has been injected in vein at the dose of 10 mg/kg.

The test Compounds of this invention have been administered 30 min. before endotoxin.

Compound No. 7, at the dose of 0.05 mmoles/kg per os, is able to protect 100% of the treated animals from the death from endotoxin.

The influence on death induced by Paraquat in the mouse.

The tests have been carried out according to C. E. Patterson (Tox., Appl. Pharm., 62, 65, 1982) and R. Linderschmidt (Tox. Appl. Pharm. 70, 105, 1983) with some modifications. The experimental plan consisted in a 3 days pretreatment with tested Compounds before Paraquat and in a 5 days treatment post Paraquat.

The Compounds were administered twice a day at 9 a.m. and 5 p.m. The activity has been expressed as effective dose ($ED_{50}$) in protecting from death 50% of the animals kept under observation for 7 days after administration of Paraquat.

Compounds Nos 1, 6, 35 and 36 have shown an $ED_{50}$ value lower than 0.1 mmoles/kg by mouth.

EXAMPLE 21

The activity of the compounds of this invention in the protection from arrhythmias from reperfusion has been evaluated in the anaesthetized rat (male rates Sprague-Dawley) according to A. J. Manning and D. Hearse, J. Mol. Cardiol., 16, 496 (1984).

The tested compounds, suspended in gumarabic, have been administered orally 90 minutes before ligating the coronary artery.

Compounds Nos 1, 2, 6, 7, 31, 33, 35, 36, 37 and 38 proved to be very effective (50–90% protection) at a dose of 0.02 mmoles/kg per os.

EXAMPLE 22

The preventing action of the Compounds of this invention on GSH depletion in vivo has been tested in the mouse, more specifically in swiss albino CD/1 females weighting 20 to 30 g. These mice were kept on an empty stomach for 16 hours before treatment. Toxicity was induced by administering 800 mg/kg of paracetamol (NAPA) via peritoneal route; this dosage induces a lethal effect in about 70% of the mice. Compounds under test were administered by mouth (2% Suspension in gumarabic) 60 minutes before NAPA.

After treatment, the mice were observed daily for two weeks.

The antagonist activity has been expressed as a percentual protection from death adjusting to 100% the percentage of deaths occured in the group of control animals treated only with NAPA.

| Compound | Dosage (μmoles/kg/os) | % Protection |
|---|---|---|
| No. 1 | 75 | 83 |
| No. 6 | 35 | 75 |
| No. 12 | 5 | 75 |
| No. 33 | 150 | 78 |
| No. 36 | 600 | 84 |

EXAMPLE 23

The following compositions, prepared according to usual methods, are illustrative of pharmaceutical dosage forms which may be prepared according to this invention.

(a) Composition for tablets

| | |
|---|---|
| Compound No. 6 | 500 mg |
| Poly vinyl pyrrolidone | 15 mg |
| Mais starch | 180 mg |
| Magnesium stearate | 5 mg |

(b) Composition for coated pills

| | | |
|---|---|---|
| Nucleous: | Compound No. 6 | 500.0 mg |
| | Poly vinyl pyrrolidone | 25.0 mg |
| | Polysorbate 80 | 5.0 mg |
| | Sodium carboxymethylstarch | 50.0 mg |
| | Magnesium stearate | 5.0 mg |
| Coating: | Hydroxy propyl methyl cellulose | 1.4 mg |
| | Poly vinyl pyrrolidone | 9.0 mg |
| | Poly ethylene glicol 4000 | 2.0 mg |
| | Talc | 39.6 mg |
| | Saccharose | 56.2 mg |
| | Magnesium carbonate | 8.4 mg |
| | Titanium dioxide | 3.4 mg |

(c) Composition for intravenous vials

| | | |
|---|---|---|
| Lyophilized: | Compound No. 6 | 30 mg |
| | Sodium bicarbonate | 15 mg |
| | Mannitol | 60 mg |
| Solvent: | water for injection | 5 ml |

(d) Composition for intravenous vials

| | | |
|---|---|---|
| Lyophilized: | Compound n. 6 | 50 mg |
| | Sodium bicarbonate | 25 mg |
| | Mannitol | 30 mg |
| Solvent: | Water for injection | 5 ml |

We claim:

1. A compound of formula

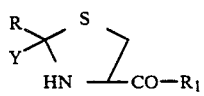

in which

Y is hydrogen, or methyl;

R is a radical selected from
   (6-methoxy-2-napthyl)-methyl,
   1-(4-isobutylphenyl)-ethyl,
   1-(6-methoxy-2-napthyl)-ethyl,
   5-(2,4-difluorophenyl)-2-hydroxyphenyl,
   2-(3-trifluoromethyl-phenylamino)-phenyl, (Z)-5-fluoro-2-methyl-1-(4-methylsulfinylbenzylidene)-1H-inden-3-yl-methyl,
1-(4-chlorobenzoyl)-5-methoxy-2-methyl-1H-indol-3-yl-methyl,
1-(3-benzoyl-phenyl)-ethyl,
2-(2,6-dichlorophenylamino)-benzyl,
1-[4-(2-thienyl-carbonyl)-phenyl]-ethyl,
when Y is hydrogen
and is 2-(6-methoxy-2-napthyl)-ethyl when Y is methyl;
$R_1$ is hydroxy, $C_1$–$C_6$ alkoxy, amino, mono- or dialkylamino, in which the alkyl has from 1 to 4 carbon atoms, or an aminoacid radical of the formula

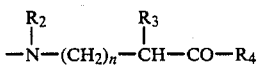

in which
$R_2$ is hydrogen; $R_3$ is hydrogen, $C_1$–$C_4$ alkyl optionally substituted by SH, SCH$_3$ or by a phenyl optionally substituted by 1 or 2 hydroxy groups;
n is an integer chosen between 0,1 and 2; when n is 0, $R_2$ and $R_3$ together may form a —(CH$_2$)$_3$—or a —CH$_2$—S—CH$_2$—group;
$R_4$ is hydroxy, $C_1$–$C_6$ alkoxy or a radical of an aminoacid of formula:

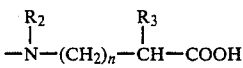

in which $R_2$, $R_3$ and n have the above-stated meanings; and their salts with pharmaceutically acceptable acids or bases.

2. A compound according to claim 1, wherein R is 1-(4-isobutylphenyl)-ethyl.

3. A compound according to claim 1, wherein R is 1-(6-methoxy-2-napthyl)-ethyl.

4. A compound according to claim 1, wherein R is 1-(3-benzoyl-phenyl)-ethyl.

5. A compound according to claim 1, wherein R is 5-(2,4-difluorophenyl)-2-hydroxyphenyl.

6. A compound according to claim 1, wherein R is 2-(3-trifluoromethyl-phenylamino)-phenyl.

7. A compound according to claim 1, wherein R is 1-(4-chlorobenzoyl)-5-methoxy-2-methyl-1H-indol-3-yl-methyl.

8. A compound according to claim 1, wherein $R_1$ is hydroxy.

9. A compound according to claim 1, wherein $R_1$ is a $C_1$–$C_6$ alkoxy group.

10. A compound according to claim 1, wherein $R_1$ is an aminoacid radical of formula

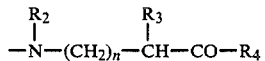

wherein
$R_2$ is hydrogen,
$R_3$ is hydrogen or a $C_1$–$C_4$ alkyl,
n is zero or one,
$R_4$ is hydroxy or a $C_1$–$C_6$ alkoxy radical.

11. A hydrochloride salt of a compound according to claim 1, wherein $R_1$ is not a hydroxy group.

12. A sodium salt of a compound according to claim 1, wherein $R_1$ or $R_4$ is hydroxy.

13. A compound according to claim 1, wherein the carbon atom at 4-position in the thiazolidine ring has configuration (R).

14. A pharmaceutical composition containing a compound according to claim 1 together with a solid or liquid pharmaceutical excipient, said compound being present in the composition in an amount effective for treating a patient showing inflammatory and painful conditions, or requiring fluidification of mucus, or for preventing arrhythmias due to reperfusion and reinfarction.

15. A method for the treatment of inflammatory and painful conditions consisting in administering to a patient in need thereof an effective amount of a compound according to claim 1.

16. A method for the treatment of pathologies requiring fluidification of mucus consisting in administering to a patient in need thereof an effective amount of a compound according to claim 1.

17. A method for preventing arrhythmias due to reperfusion and reinfarction consisting in administering to a patient in need thereof an effective amount of a compound according to claim 1.

* * * * *